(12) United States Patent
Jepsen et al.

(10) Patent No.: US 11,602,470 B2
(45) Date of Patent: *Mar. 14, 2023

(54) SYSTEMS AND METHODS FOR MOUNTING MEDICAL EQUIPMENT

(71) Applicant: Cadwell Laboratories, Inc., Kennewick, WA (US)

(72) Inventors: David Lee Jepsen, Kennewick, WA (US); Richard A. Villarreal, West Richland, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/186,603

(22) Filed: Feb. 26, 2021

(65) Prior Publication Data

US 2021/0251831 A1  Aug. 19, 2021

Related U.S. Application Data

(60) Continuation of application No. 16/376,856, filed on Apr. 5, 2019, now Pat. No. 10,959,895, which is a division of application No. 15/486,623, filed on Apr. 13, 2017, now Pat. No. 10,292,883.

(51) Int. Cl.
| | |
|---|---|
| *A61G 7/05* | (2006.01) |
| *A61B 50/28* | (2016.01) |
| *F16M 11/08* | (2006.01) |
| *A61B 90/57* | (2016.01) |
| *A61G 13/10* | (2006.01) |

(Continued)

(52) U.S. Cl.
CPC ............ *A61G 7/0503* (2013.01); *A61B 50/28* (2016.02); *A61B 90/50* (2016.02); *A61B 90/57* (2016.02); *A61G 13/101* (2013.01); *F16M 11/08* (2013.01); *F16M 13/022* (2013.01); *A61B 2090/571* (2016.02); *F16M 13/02* (2013.01)

(58) Field of Classification Search
CPC .... A61G 7/0503; A61G 13/101; A61B 50/28; A61B 90/50; A61B 90/57; F16M 11/08; F16M 13/02
USPC ..... 248/228.3, 228.4, 228.6, 229.23, 229.25, 248/229.13, 229.15, 231.51, 231.71, 248/316.1, 220.21, 222.11, 304
See application file for complete search history.

(56) References Cited

U.S. PATENT DOCUMENTS

| | | | |
|---|---|---|---|
| 6,805,668 B1 | 10/2004 | Cadwell | |
| 6,870,109 B1 * | 3/2005 | Villarreal | ................ A61B 5/24 174/102 R |
| 7,072,521 B1 | 7/2006 | Cadwell | |

(Continued)

*Primary Examiner* — Todd M Epps
(74) *Attorney, Agent, or Firm* — Novel IP

(57) ABSTRACT

Systems, devices and methods are described for mounting medical equipment on IV poles, bed rails and other supporting structures in medical facilities including operating rooms and critical care sections. A system including a mounting hanger and corresponding equipment housing is disclosed that allows quick mounting and dismounting of equipment from a supporting structure. The novel structural design of mounting hanger including a symmetrical t-slot feature and a plunger lock allows a piece of equipment to be mounted on a supporting structure in multiple orientations as per the requirement which allows a user to optimize the placement of equipment in the medical environment.

18 Claims, 13 Drawing Sheets

(51) Int. Cl.
*F16M 13/02* (2006.01)
*A61B 90/50* (2016.01)

(56) References Cited

U.S. PATENT DOCUMENTS

| | | | | |
|---|---|---|---|---|
| 7,230,688 | B1 * | 6/2007 | Villarreal | A61B 5/14551 |
| | | | | 250/206 |
| 7,374,448 | B2 * | 5/2008 | Jepsen | H01R 13/6275 |
| | | | | 439/350 |
| 7,546,993 | B1 * | 6/2009 | Walker | F16M 13/022 |
| | | | | 248/229.12 |
| 7,914,350 | B1 | 3/2011 | Bozich | |
| D670,656 | S | 11/2012 | Jepsen | |
| 8,695,957 | B2 * | 4/2014 | Quintania | B25B 5/006 |
| | | | | 269/74 |
| 9,121,423 | B2 * | 9/2015 | Sharpe | F16M 13/022 |
| 9,155,503 | B2 * | 10/2015 | Cadwell | A61B 8/5261 |
| 9,295,401 | B2 * | 3/2016 | Cadwell | A61B 5/389 |
| 9,714,350 | B2 * | 7/2017 | Hwang | C09D 7/61 |
| 9,730,634 | B2 * | 8/2017 | Cadwell | A61B 34/10 |
| 9,999,719 | B2 * | 6/2018 | Kitchen | A61M 5/1415 |
| 10,292,883 | B2 * | 5/2019 | Jepsen | A61G 13/101 |
| 10,959,895 | B2 * | 3/2021 | Jepsen | A61B 50/28 |
| 2014/0121555 | A1 | 5/2014 | Scott | |
| 2014/0275926 | A1 | 9/2014 | Scott | |
| 2016/0000382 | A1 | 1/2016 | Jain | |
| 2016/0174861 | A1 | 6/2016 | Cadwell | |

* cited by examiner

SYSTEMS AND METHODS FOR MOUNTING MEDICAL EQUIPMENT

CROSS-REFERENCE

The present application is a continuation application of U.S. patent application Ser. No. 16/376,856, entitled "Systems and Methods for Mounting Medical Equipment" and filed on Apr. 5, 2019, which is a division application of U.S. patent application Ser. No. 15/486,623, entitled "System and Method for Mounting Medical Equipment", filed on Apr. 13, 2017, and issued as U.S. Pat. No. 10,292,883 on May 21, 2019, both of which are herein incorporated by reference in their entirety.

FIELD

The present specification generally relates to the field of mounting medical equipment on support structures proximate to patients and more specifically to a quick and tool-less system and method of mounting medical equipment in multiple orientations.

BACKGROUND

Hospitalized patients often require patient care equipment to be in close proximity during their hospital stay. Such patient care equipment may include any one or more of the following: service connectors, heart monitors, defibrillators, infusion pumps, equipment monitors and other medical instruments, many of which directly connect to the patient via lines or tubes. Some of the service connectors may be medical gas connectors to provide medical gases, such as oxygen, nitrogen, and air. Service connectors may also include electrical power outlets to supply electrical power and medical gas connectors to provide medical gases, such as oxygen, nitrogen, and air. Some of the service connectors may be data communication ports to receive and transmit data, such as, for example, audio, video, and patient information.

The medical equipment is typically mounted in an operating room, emergency room, critical care room, lab area or the like, to an overhead mounting structure attached to the overhead building structure. The mounting structure is typically custom-designed, fabricated and permanently welded or affixed to an existing overhead building structure. Alternatively, the equipment may be mounted with the help of mounting hangers which are connected to surgical beds, IV poles or other supporting structures. The mounting hangers typically used for attaching the equipment with surgical beds, IV poles or other supporting structures, however, do not provide much operational flexibility to a user. In most of the commercially available mounting solutions, a bed rail hanger bracket is permanently affixed to equipment housings and cannot be user adjusted or optimized in any way. In mounting systems that do provide a limited degree of flexibility in changing the position of the mounted equipment, the process of removal and repositioning of the equipment is highly cumbersome. The equipment is typically coupled to mounting hangers through fastening means such as screws and nuts, which makes the process of attaching/detaching the equipment from a mounting hanger very time consuming. The process involves tools to disengage the fastening means and detach the equipment from a mounting hanger and then to attach the equipment to the mounting hanger in a different position and then reengage the fastening means.

The typical commercially available mounting hangers are not symmetrical about a connecting portion or the locking access area within a corresponding equipment housing. As a result, the equipment can be engaged in only one specific orientation. Restrictions with mounting the medical equipment in a specific orientation do not allow the user to optimize the placement of medical equipment in the operating area. As a result, many times, the intravenous lines, tubes and wires coupled to the medical equipment are left to dangle or hang between patient care equipment and the patient.

The medical equipment is placed inside a housing comprising the means/receivers to engage with a corresponding set of mounting hangers. The typical housing used to receive the medical equipment is bulky and the receivers are also prominently visible. Further, the receivers are not designed in a symmetrical shape that would allow for the mounting of equipment in multiple orientations.

Further, in currently available mounting hangers, vertical movement of the equipment, such as raising or lowering the equipment level relative to a bed surface, is not easy as it involves disengaging a mounting hanger from a surgical bed or supporting structure and then, if the configuration permits, re-engaging the mounting hanger at the desired height. Typically, a technician has to remove the medical equipment from a mounting hanger before changing the vertical position of the hanger, which in itself is a very tedious process.

Therefore, there is a need for a quick and tool-less solution for mounting equipment (medical or other) to surgical beds, IV poles or other support structures in a variety of orientations, allowing the user to optimize the orientation for the most efficient routing of electronic cables and/or patient leads emanating from the equipment. There is also a need for solutions that allow for quick connection and disconnection of a piece of equipment from a corresponding mounting hanger. There is also a need for mounting solutions in which a connecting portion or the locking access area in the equipment housing is symmetrical in design and allows engaging the equipment in multiple orientations. There is also a need for equipment housings that have multiple sets of receivers for engaging with the mounting hangers and thus, allowing for quick vertical repositioning of the equipment.

SUMMARY

The present specification discloses a system for mounting medical equipment on a support structure comprising: a plurality of mounting hangers, each of the plurality of mounting hangers comprising a hook portion configured to couple with the support structure and a substantially straight portion wherein said substantially straight portion comprises a protruding section and a plunger lock; and a housing, wherein the housing is attached to the medical equipment and comprises a plurality of receiver sections on an external surface of said housing and wherein each of the plurality of receiver sections is configured to receive and mate with a corresponding protruding section of each of said plurality of mounting hangers, wherein said plunger lock is configured to lock said protruding section with said receiver section.

Optionally, said protruding section comprises a t-slot portion. Optionally, each of the plurality of receiver sections comprises an opening and a locking access area wherein said protruding section is configured to be first received in said opening and subsequently slid to mate with the locking access area. Optionally, when the protruding section is positioned in a final mated position with the locking access area, the plunger lock is configured to be centered over an accommodating hole in the receiver section and automatically engaged therein, thereby locking one of said plurality of mounting hangers with the receiver section of the housing. The locking access area may comprise a hole to receive a portion of the plunger lock to thereby automatically lock one of said plurality of mounting hangers with said receiver section.

Optionally, said plurality of mounting hangers are coupled to an equal and corresponding number of receiver sections in the housing.

Optionally, the plunger lock is configured to be manually retracted against spring loaded pressure in order to detach one of said plurality of mounting hangers from the housing.

Optionally, said t-slot portion is configured to be rotated symmetrically about an axis prior to being received in said opening and subsequently slid to mate with the locking access area of said receiver section. Each of said plurality of mounting hangers may be configured to be connected to said housing in more than one orientation.

Optionally, said hook portion and said substantially straight portion of the mounting hanger are connected through a connecting portion. The hook portion, said substantially straight portion and said connecting portion of each of said plurality of mounting hangers may be a single unitary, molded component.

Each of said plurality of mounting hangers and said receiver section in the housing may comprise metal. Optionally, said mounting hanger and said receiver sections in the housing are manufactured using plastic for applications requiring low strength.

Optionally, said plunger lock comprises a spring.

Each of said plurality of mounting hangers may be configured to be disengaged from a corresponding receiver section of the housing by manually retracting the plunger lock against a spring without requiring a tool to assist in the manual retraction of said plunger lock.

Optionally, said support structure comprises at least one of an IV pole and bed rail.

The system may be deployed for efficient placement of equipment in medical facilities or at home during pre or post operating care of patients.

The present specification also discloses a system for mounting medical equipment on at least one of an IV pole or bed rail comprising: at least one mounting hanger comprising a hook portion configured to couple the at least one mounting hanger with the IV pole or bed rail and a substantially straight portion wherein said straight portion comprises a protruding section and a plunger lock; and a housing configured to accommodate the medical equipment therein, wherein the housing comprises at least one receiver section on an external surface of said housing, wherein the at least one receiver section comprises a first section and a second section, is configured to receive the protruding section of the at least one mounting hanger in the first section, and is configured to permit said received at least one mounting hanger to be slid to mate with the second section such that the plunger lock is configured to align with an accommodating hole in the second section and automatically engage the accommodating hole to lock the at least one mounting hanger with the at least one receiver section.

The present specification also discloses a method of mounting medical equipment on a support structure comprising: positioning the medical equipment inside an equipment housing comprising at least one receiver section; coupling at least one mounting hanger with the at least one receiver section in the equipment housing, wherein coupling said mounting hanger with the at least one receiver section comprises inserting a t-slot protruding portion of said mounting hanger in an opening of the at least one receiver section and sliding the at least one mounting hanger to mate the t-slot protruding portion with a locking access area in the at least one receiver section, wherein, as the t-slot protruding section is slid into a final mated position with the locking access area, a plunger lock located on the at least one mounting hanger automatically engages with a hole in the at least one receiver section to lock the at least one mounting hanger with the at least one receiver section; and coupling said at least one mounting hanger with said support structure.

Optionally, coupling said at least one mounting hanger with said support structure is performed before coupling said at least one mounting hanger with the at least one receiver section in the equipment housing.

The present specification also discloses a system for mounting medical equipment on a supporting structure comprising: at least one mounting hanger comprising a first straight portion configured to couple the at least one mounting hanger with the supporting structure and a second straight portion wherein said second straight portion comprises a protruding section and a plunger lock; and a housing comprising at least one receiver section on an external surface of the housing with the at least one receiver section configured to receive and mate with the protruding section of the at least one mounting hanger, wherein said plunger lock is configured to lock said protruding section of the at least one mounting hanger with said at least one receiver section.

Optionally, said supporting structure comprises an IV pole and said mounting hanger is configured to be mounted on the IV pole using a pole mounting clamp. Optionally, said first straight portion comprises at least one hole or opening configured to couple the at least one mounting hanger with said pole mounting clamp.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1A:
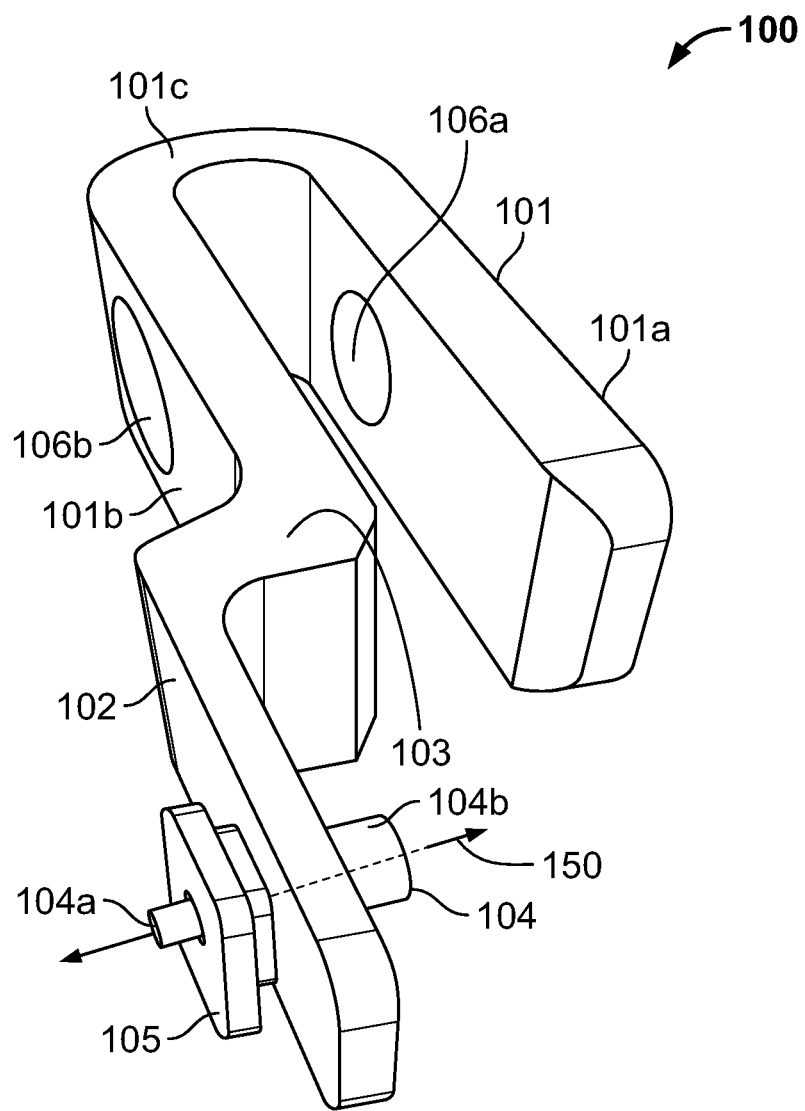
FIG. 1A is a pictorial representation of a mounting hanger in accordance with an embodiment of the present specification.

The present specification is directed towards a system and method for efficient management of medical equipment required in close proximity of patients during a hospital stay or during pre/post-operative medical care at home. In embodiments, the present specification describes a novel equipment mounting solution for mounting medical equipment on surgical beds, IV poles or other supporting structures. The equipment mounting solution disclosed in the present specification solves several shortcomings present in existing equipment mounting systems.

In addition, the present specification discloses a system comprising a mounting hanger and corresponding equipment housing that allows for quick mounting and dismounting of equipment from a support structure. In embodiments, a piece of equipment is placed inside an equipment housing which comprises a plurality of receiver sections, each receiver section configured to receive and engage a corresponding mounting hanger. The novel structural designs of mounting hangers and receiver sections are configured on the external surface of the equipment housing allowing for a piece of equipment to be mounted on a supporting structure in multiple orientations, in turn, allowing a user to optimize the placement of equipment in a medical environment. In contrast, in typical prior art mounting systems, it is not possible to mount the equipment in multiple orientations because of design constraints. In existing systems, a mounting hanger can be engaged with the equipment or equipment housing in only one specific orientation in accordance with the structural design of mounting hanger. A novel connection mechanism for attaching or locking a mounting hanger to equipment housing, which ensures that the removal and re-orientation of mounting hangers is a tool-less and quick operation, is also disclosed.

In embodiments, a piece of equipment is placed inside an equipment housing that comprises a plurality of receiver sections each configured to receive and engage a mounting hanger. In embodiments, the mounting hanger comprises a hook portion and a straight portion wherein the hook portion is configured to hang or couple the mounting hanger to support structures, including but not limited to, IV poles and bed rails, while the straight portion is configured to couple the mounting hanger to equipment housing. In embodiments, the straight portion of a mounting hanger comprises a unique t-slot portion with a plunger lock for positive locking of the hanger onto a corresponding receiver section configured on an external surface of the equipment housing.

In embodiments, the mounting hangers are configured to automatically engage and lock with the receiver sections of the equipment housing. Locking is accomplished via the inclusion of a spring loaded plunger lock on the mounting hanger which is configured to align with, and be seated within, a receiving hole in the receiver section of the equipment housing when the mounting hanger and equipment housing are coupled. In various embodiments, the hole comprises any one of a void, indentation, or space that can receive, and physically engage, with a member, wherein the member comprises a portion of the plunger lock. When the t-slot portion of the mounting hanger is slid into a receiver section of the equipment housing, the spring mechanism of the plunger lock causes the lock to automatically engage with the receiving hole. The automatic locking prevents the mounting hanger from inadvertently disengaging from the equipment housing. A user must manually pull the plunger to disengage the spring loaded plunger lock, allowing for separation of the mounting hanger from the equipment housing by sliding the t-slot portion of the mounting hanger out of the receiver section. No additional tools are required to disengage the spring loaded plunger lock and separate the mounting hanger from the equipment housing.

In embodiments, the t-slot portion of the mounting hanger and the associated locking access area in the receiver section of equipment housing, share an equivalent symmetrical shape. For example, in an embodiment, the t-slot portion of the mounting hanger and locking access area in the receive section are both square in shape. The symmetrical shape allows the user to rotate the mounting hanger about an axis, for example, a series of 90 degree rotations for a square shaped t-slot portion, and then couple the mounting hanger with the locking access area, thus allowing the hanger to be coupled with the equipment housing in multiple orientations. In embodiments, a piece of equipment can be mounted on the support structure in at least one vertical orientation or at least one horizontal orientation.

In embodiments, the equipment housing comprises multiple receiver sections configured at different vertical levels which allow a user to mount a piece of equipment at different vertical levels. In embodiments, to raise or lower the vertical level of equipment from the ground, a user can quickly remove the equipment from the mounting hanger and re-engage the mounting hanger with an alternate receiver section positioned at the desired vertical level.

In embodiments, equipment can be mounted on a support structure using one or more mounting hangers. The number of mounting hangers used for mounting a specific piece of equipment depends on a variety of factors, including but not limited to, weight, volume and dimensions of the equipment and structure, strength and type of the mounting hanger.

Embodiments disclosed in this specification provide a quick and tool-less way to mount equipment (medical or any other) to surgical beds, IV poles or other support structures in a variety of orientations. The above flexibility helps to optimize the orientation for the most efficient routing of various electronic cables and/or patient leads emanating from a piece of equipment.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

FIG. 1A shows a mounting hanger 100 in accordance with an embodiment of the present specification. As shown in FIG. 1A, the mounting hanger 100 comprises a first portion 101 coupled to a second portion 102 through a connecting portion 103.

In embodiments, the first portion 101 is structured in the form of a substantially u-shaped hook comprising a first straight portion 101a connected to a second straight portion 101b through a curved connecting portion 101c. The hook portion 101 is used to hang or couple the mounting hanger 101 on or with support structures including, but not limited to a, surgical bed rail or an IV pole. In some embodiments, the mounting hanger 100 also comprises at least two openings or holes 106a and 106b for hanging the hook portion 101 from supporting structures, including but not limited to, bed rails via plastic ties, chains or other non-rigid means. In an embodiment, opening or hole 106a is located on the first straight portion 101a of hook 101 and hole 106b is located on the second straight portion 101b of hook 101.

The second portion 102 of mounting hanger 100 is used for connecting or engaging the mounting hanger 100 with equipment housing. In an embodiment, the second portion 102 is a straight flat component comprising a coupling portion 105, which has the form of a t-slot shaped protrusion and is used to couple the mounting hanger 100 with a corresponding t-slot shaped receiver section in the equipment housing, and a lock 104, which is used to lock the mounting hanger 100 with said receiver section.

In medical applications, durability of a lock or connection between the mounting hanger and the equipment housing is critical in preventing the equipment from falling and being damaged. In embodiments of the present specification, the lock 104 comprises a positive locking mechanism in which a connection between the mounting hanger and the equipment housing does not become loose due to vibrations. In embodiments, the lock 104 comprises a spring loaded plunger lock which can be quickly unlocked/locked through a manual pull and release operation.

In an embodiment, equipment is placed within the equipment housing which comprises a plurality of receiver sections each adapted to receive a coupling portion 105 comprising a t-slot shaped protrusion and a portion of lock 104 of a corresponding mounting hanger. In an embodiment, the coupling portion 105 is first inserted into an opening provided in a receiver section on the equipment housing and is then slid into a locking access area in the receiver section. Both the receiver section opening and locking access area share the symmetrical shape of the coupling portion 105. The locking access area further comprises a t-slot for receiving the t-slot shaped protrusion of the coupling portion 105. In some embodiments, the receiver section opening is sized larger than the locking access area and does not include a t-slot. Once the coupling portion 105 settles into the locking access area with the receiver section, the plunger lock 104 engages with the receiver section and locks the mounting hanger with the equipment housing. In embodiments, a locking section 104a of the plunger lock 104, present on a second side of second portion 102 opposite a first side having a handle section 104b of the plunger lock, is received in a corresponding plunger hole present in the receiver section which locks the mounting hanger with the equipment housing. This prevents the hanger 100 from accidently disengaging itself from the equipment. In embodiments, a user can retract the spring plunger lock 104 manually by pulling on the handle section 104b to release the hanger 100 for quick removal or repositioning of equipment.

In embodiments, the coupling portion 105 of the mounting hanger 100 is symmetrical in shape and shares the same shape as a locking access area in a receiver section of equipment housing. In embodiments, the symmetrical shape of the coupling portion 105 allows for rotation of the mounting hanger 100 about an axis 150. The mounting hanger 100 may be rotated about axis 150, when the coupling portion 105 is not coupled to the receiver section, and then may be slid into the locking access area for coupling. In an embodiment comprising a square shaped coupling portion and square shaped corresponding locking access area, the mounting hanger is configured to be rotated through a series of four orientations, each orientation comprising a 90 degree rotation, either in a clockwise or counter clockwise direction, from the previous orientation. For example, in an embodiment, a first orientation is normal to the ground, a second orientation is rotated 90 degrees in a clockwise direction and perpendicular to the first orientation, a third orientation is rotated 90 degrees further in a clockwise direction, perpendicular to the second orientation, and flipped 180 degrees relative to the first orientation, and a fourth orientation is rotated 90 degrees further in a clockwise direction, perpendicular to the third and first orientations, and flipped 180 degrees relative to the second orientation. Thus, the coupling portion 105 can be coupled to the equipment housing in multiple orientations. Flexibility to couple the hanger 100 with a receiver section of equipment housing in multiple orientations means that a user can mount the equipment in multiple orientations, including at least one horizontal orientation and at least one vertical orientation.

In embodiments, the first portion 101, the second portion 102 and the connecting portion 103 are seamlessly coupled to each other. In embodiments, the first portion 101, the second portion 102 and the connecting portion 103 are parts of a single structure manufactured using injection molding.

In embodiments, for higher strength requirements, the coupling portion 105 and the corresponding receiver sections within the equipment housing are manufactured using metal. For lower strength or lower cost requirements, plastic or other materials may be used. In embodiments, each mounting hanger is configured to support a weight of at least 48 pounds without breaking or becoming disengaged from the receiver sections of the equipment housing. In an embodiment in which two mounting hangers are used simultaneously, the pair of mounting hangers is configured to support a weight of at least 96 pounds without breaking or becoming disengaged from the receiver sections of the equipment housing.

In embodiments, hanger 100 may include various alternate shapes, configurations and geometries and still be capable of mounting to a piece of equipment as long as the quick release coupling portion 105, or variations thereof, are provided in the hanger 100.

Figure 1B:
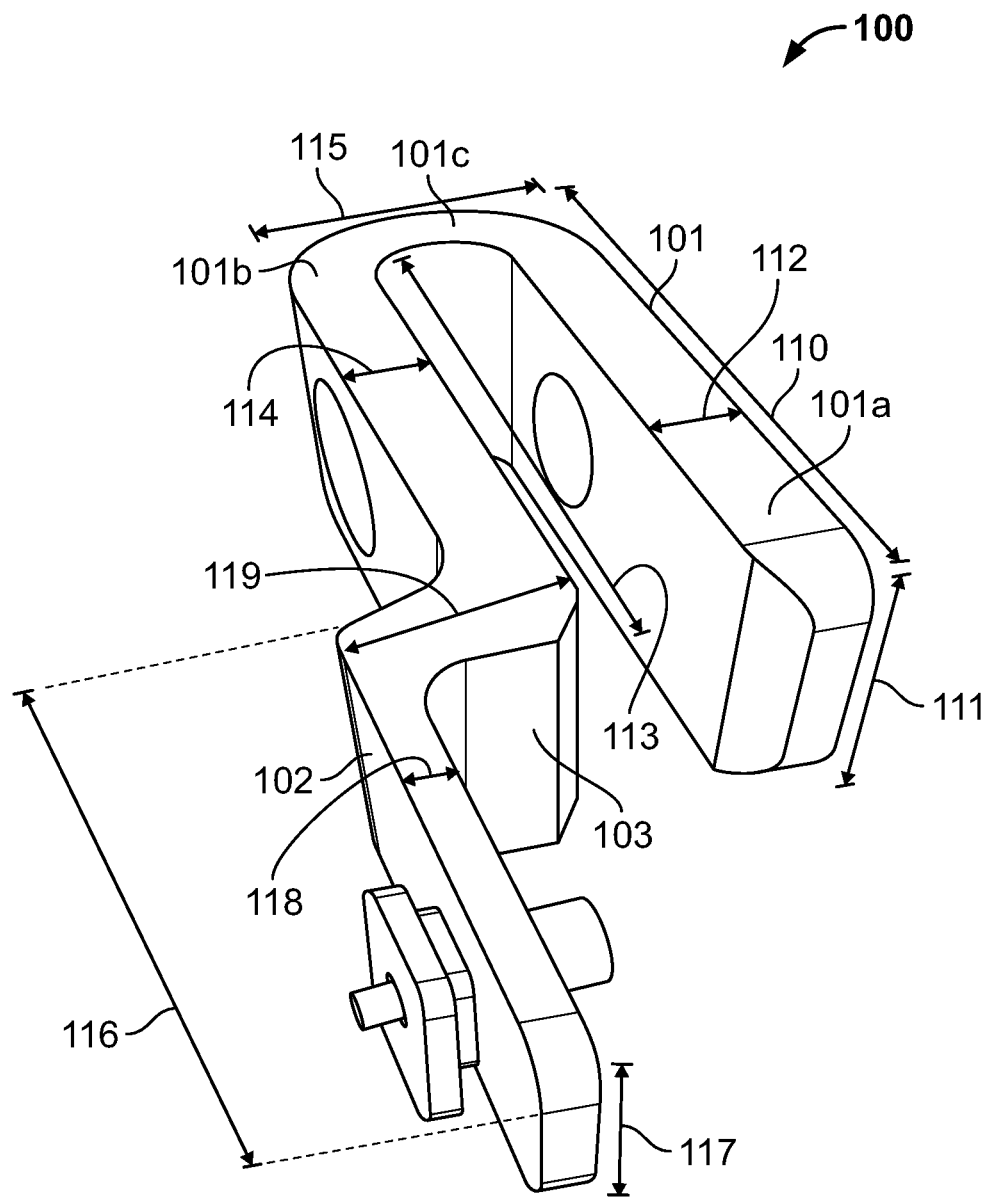
FIG. 1B illustrates the various dimensions of the mounting hanger of FIG. 1A.

FIG. 1B illustrates the dimensions of various portions of the mounting hanger of FIG. 1A. As shown in FIG. 1B, the mounting hanger 100 comprises a first portion 101 coupled to a second portion 102 through a connecting portion 103. In embodiments, the first portion 101 is structured in the form of a hook comprising a first straight portion 101a connected to a second straight portion 101b through a curved connecting portion 101c. In an embodiment, the length 110, the width 111 and the thickness 112 of the first straight portion 101a are 1.95 inches, 1.00 inches and 0.25 inches respectively. In an embodiment, the length 113 and the thickness 114 of the second straight portion 101b are 1.95 inches and 0.25 inches respectively. The width of the second straight portion 101b is equal to the width of the first straight portion 101a in an embodiment. In an embodiment, the diameter 115 of the curved connecting portion 101c is 0.905 inches. In an embodiment, the length 116, the width 117 and the thickness 118 of straight portion 102 are 1.423 inches, 1.00 inches and 0.125 inches respectively. In an embodiment, the length 119 of the connecting portion 103 is equal to 0.585 inches.

Figure 1C:
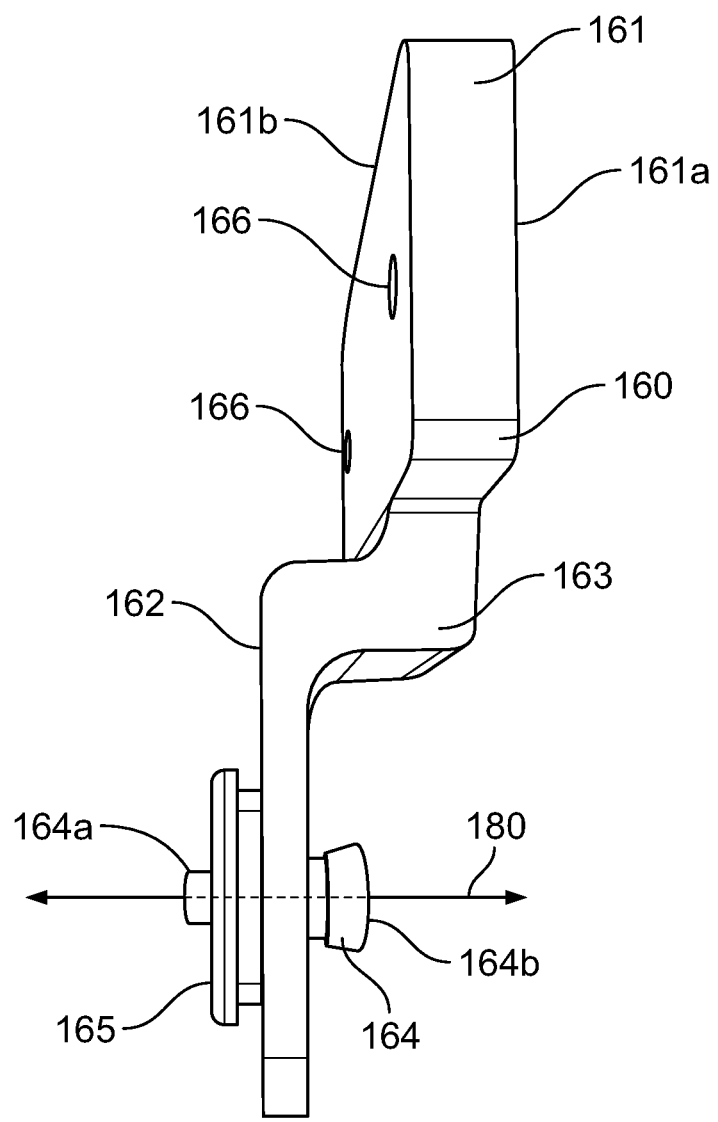
FIG. 1C is a pictorial representation of a mounting hanger in accordance with another embodiment of the present specification.

FIG. 1C shows a mounting hanger in accordance with another embodiment of the present specification. As shown in FIG. 1C, the mounting hanger 160 comprises a first portion 161 coupled to a second portion 162 via a connecting portion 163. In embodiments, the first portion 161 is structured in the form of a cuboid having a rectangular first surface 161a and a rectangular second surface 161b opposite said first surface 161a. In embodiments, the mounting hanger 160 is used for mounting the medical equipment on supporting structures, such as IV poles, with the help of a pole mounting clamp. The first portion 161 of the mounting hanger comprises at least one, and preferably, two openings or threaded screw holes 166 which are configured to couple the mounting hanger 160 with a corresponding pole mounting clamp via screws or other such means. The second portion 162 of mounting hanger 160 is used for connecting or engaging the mounting hanger 160 with equipment housing. In an embodiment, the second portion 162 is a straight flat component comprising a coupling portion 165, which has the form of a t-slot shaped protrusion and is used to couple the mounting hanger with a corresponding t-slot shaped receiver section in the equipment housing, and a lock 164, which is used to lock the mounting hanger 160 with said receiver section.

In medical applications, durability of a lock or connection between the mounting hanger and the equipment housing is critical in preventing the equipment from falling and being damaged. In embodiments of the present specification, the lock 164 comprises a positive locking mechanism in which a connection between the mounting hanger and the equipment housing does not become loose due to vibrations. In embodiments, the lock 164 comprises a spring loaded plunger lock which can be quickly unlocked/locked through a manual pull and release operation.

In an embodiment, equipment is placed within the equipment housing which comprises a plurality of receiver sections each adapted to receive a coupling portion 165 comprising a t-slot shaped protrusion and a portion of lock 164 of a corresponding mounting hanger. In an embodiment, the coupling portion 165 is first inserted into an opening provided in a receiver section on the equipment housing and is then slid into a locking access area in the receiver section. The opening and locking access area share the symmetrical shape of the coupling portion 165. The locking access area further comprises a t-slot for receiving the t-slot shaped protrusion of the coupling portion 165. In some embodiments, the receiver section opening is sized larger than the locking access area and does not include a t-slot. Once the coupling portion 165 settles into the locking access area with the receiver section, the plunger lock 164 automatically engages to lock the mounting hanger with the locking access area of receiver section. The base of the locking access area of the receiver section comprises an accommodating hole that receive a protruding section 164a of the lock 164 which locks the two units and prevents the mounting hanger from disengaging itself from the equipment. In embodiments, locking section 164a is present on a second side of second portion 162 opposite a first side having a handle section 164b of the plunger lock. This prevents the hanger 160 from accidently disengaging itself from the equipment. In embodiments, a user can retract the spring loaded plunger lock 164 manually by pulling on the handle section 164b to release the hanger 160 for quick removal or repositioning of equipment.

In embodiments, the coupling portion 165 of the mounting hanger 160 is symmetrical in shape and shares a same shape with a locking access area in a receiver section of equipment housing. In embodiments, the symmetrical shape of the coupling portion 165 allows for rotation of the mounting hanger 160 about an axis 180. The mounting hanger 100 may be rotated about axis 180, while the coupling portion 165 is not coupled to the receiver section, and then may be slid into the locking access area for coupling. Thus, the coupling portion 165 can be coupled to the equipment housing in multiple orientations. Flexibility to couple the hanger 160 with a receiver section of equipment housing in multiple orientations means that a user can mount the equipment in multiple orientations, including at least one horizontal orientation and at least one vertical orientation.

In embodiments, the first portion 161, the second portion 162 and the connecting portion 163 are seamlessly coupled to each other. In embodiments, the first portion 161, the second portion 162 and the connecting portion 163 are parts of a single structure manufactured using injection molding.

In embodiments, for higher strength requirements, the coupling portion 165 and the corresponding receiver sections within the equipment housing are manufactured using metal. For lower strength or lower cost requirements, plastic or other materials may be used.

Figure 1D:
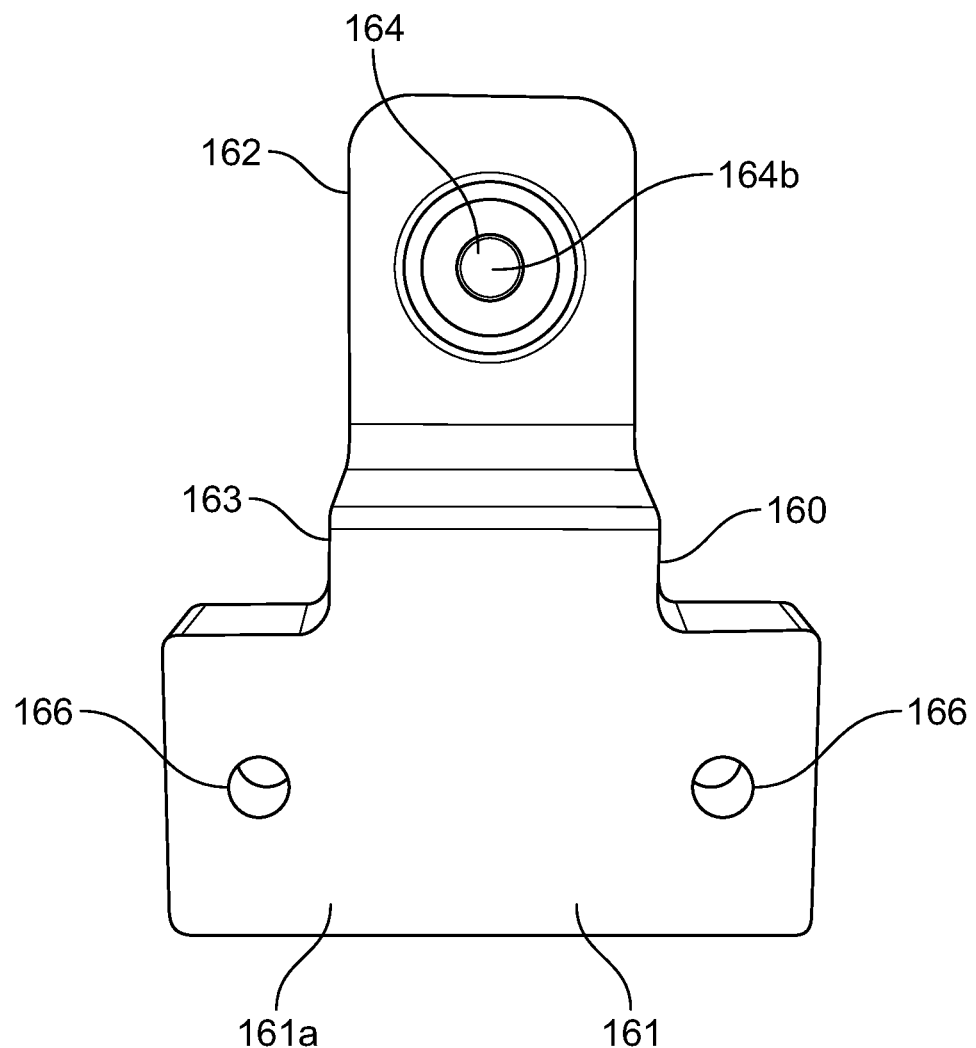
FIG. 1D is a pictorial representation of the mounting hanger of FIG. 1C oriented with the second portion above the first portion and viewed from a first side.

FIG. 1D shows the mounting hanger of FIG. 1C oriented with the second portion 162 positioned above the first portion 161 and viewed from a first side. As shown in FIG. 1D, the mounting hanger 160 comprises a first portion 161 coupled to a second portion 162 through a connecting portion 163. The first portion 161 comprises a rectangular first surface 161a. Accommodating holes or openings 166 are provided in the first portion 161 which are used to couple the mounting hanger 160 with supporting structures such as IV poles. In embodiments, the supporting structure, such as an IV pole, comprises a pole mounting clamp and the mounting hanger 160 is coupled to the pole mounting clamp with the help of screws that pass through the threaded holes

166. The handle section 164b of the plunger lock 164 is visible in the second portion 162. In the embodiment shown in FIG. 1D, the plunger lock 164 is shown in a locked or depressed position.

Figure 1E:
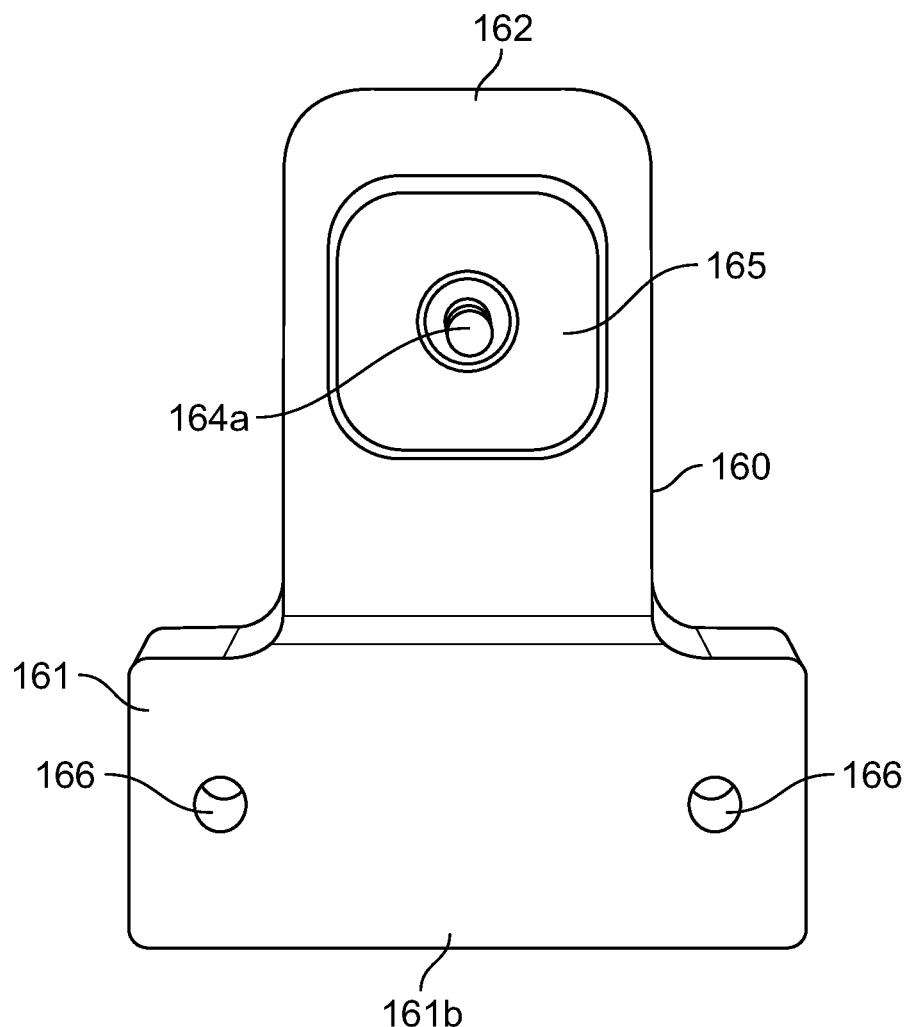
FIG. 1E is a pictorial representation of the mounting hanger of FIG. 1C oriented with the second portion above the first portion and viewed from a second side.

FIG. 1E shows the mounting hanger of FIG. 1C oriented with the second portion 162 above the first portion 161 and viewed from a second side opposite the first side shown in FIG. 1D. As shown in FIG. 1E, a second surface 161b of the first portion 161 comprises two openings or holes 166 for coupling the mounting hanger 160 to supporting structures, such as IV poles, via pole mounting clamps and screws. The second portion 162 comprises a coupling portion 165 comprising a t-slot shaped protrusion, which is used to couple the mounting hanger with a corresponding t-slot shaped receiver section in the equipment housing. The locking portion 164a of the plunger lock 164 is visible in the second portion 162 of the mounting hanger 160.

Figure 1F:
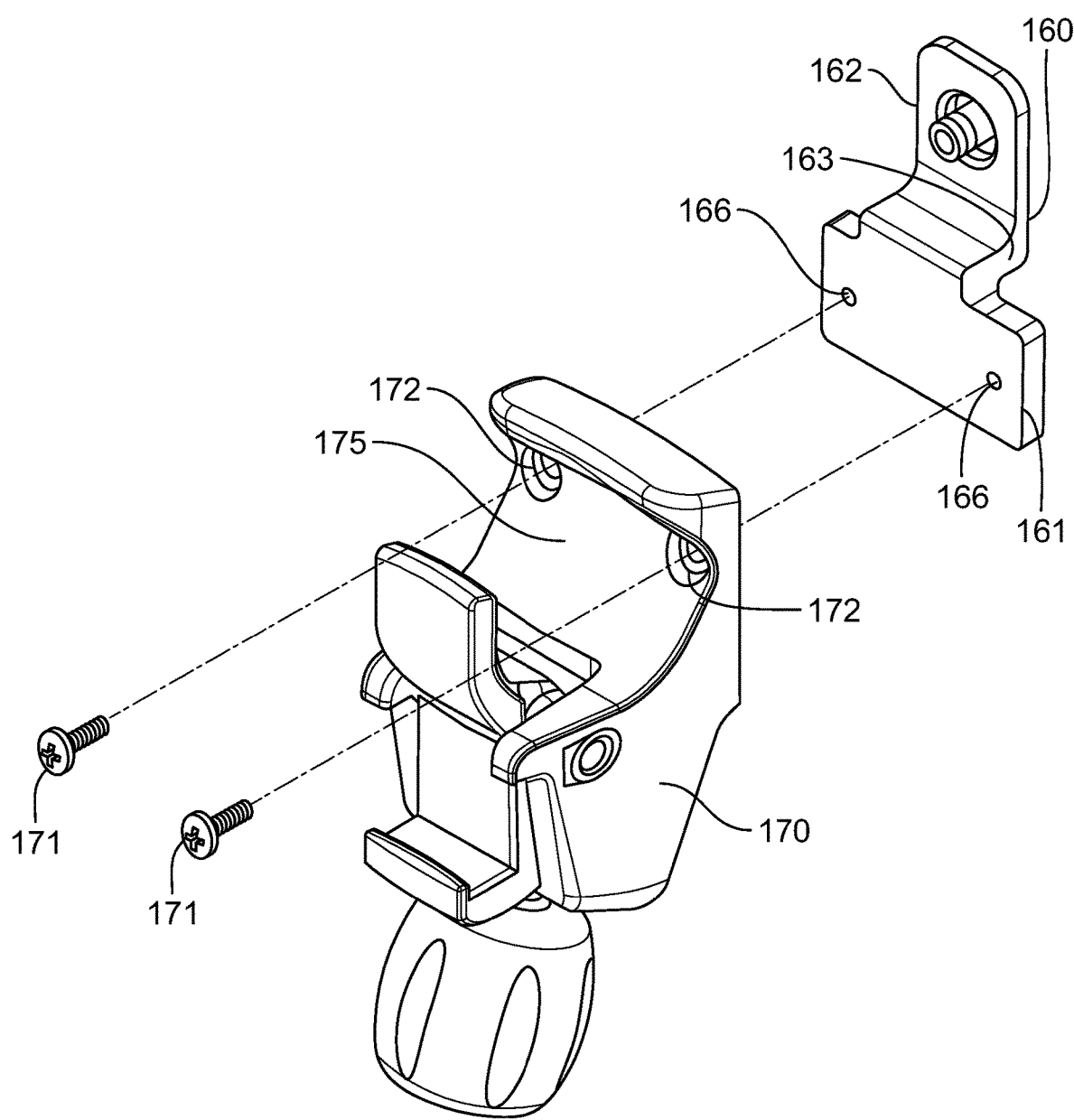
FIG. 1F illustrates the mounting hanger of FIG. 1C and a corresponding pole mounting clamp in accordance with an embodiment of the present specification.

FIG. 1F illustrates the mounting hanger 160 of FIG. 1C and a corresponding pole mounting clamp 170 in accordance with an embodiment of the present specification. As shown in FIG. 1F, the mounting hanger 160 comprises a first portion 161 coupled to a second portion 162 via a connecting portion 163. Accommodating threaded holes or openings 166 are provided in the first portion 161 which are used to couple the mounting hanger 160 with supporting structures such as IV poles. In embodiments, the supporting structure, such as an IV pole, comprises a pole mounting clamp 170 and the mounting hanger 160 is coupled to the pole mounting clamp 170 with the help of screws 171 that pass through the threaded holes 166. An exemplary pole mounting clamp 170 is depicted in FIG. 1F. The clamp 170 comprises a pair of openings or threaded holes 172 which are aligned with the openings or holes 166 on the mounting hanger. Subsequently, a pair of screws are 171 are passed through the holes 172 and 166 to lock the two components (mounting hanger 160 and clamp 170) with each other. As shown in FIG. 1F, the pole mounting claim 170 comprises an open area 175 within which a portion of IV pole is received. In embodiments, the pole mounting clamp 170 is first coupled to the mounting hanger and is then subsequently engaged with an IV pole.

Figure 2:
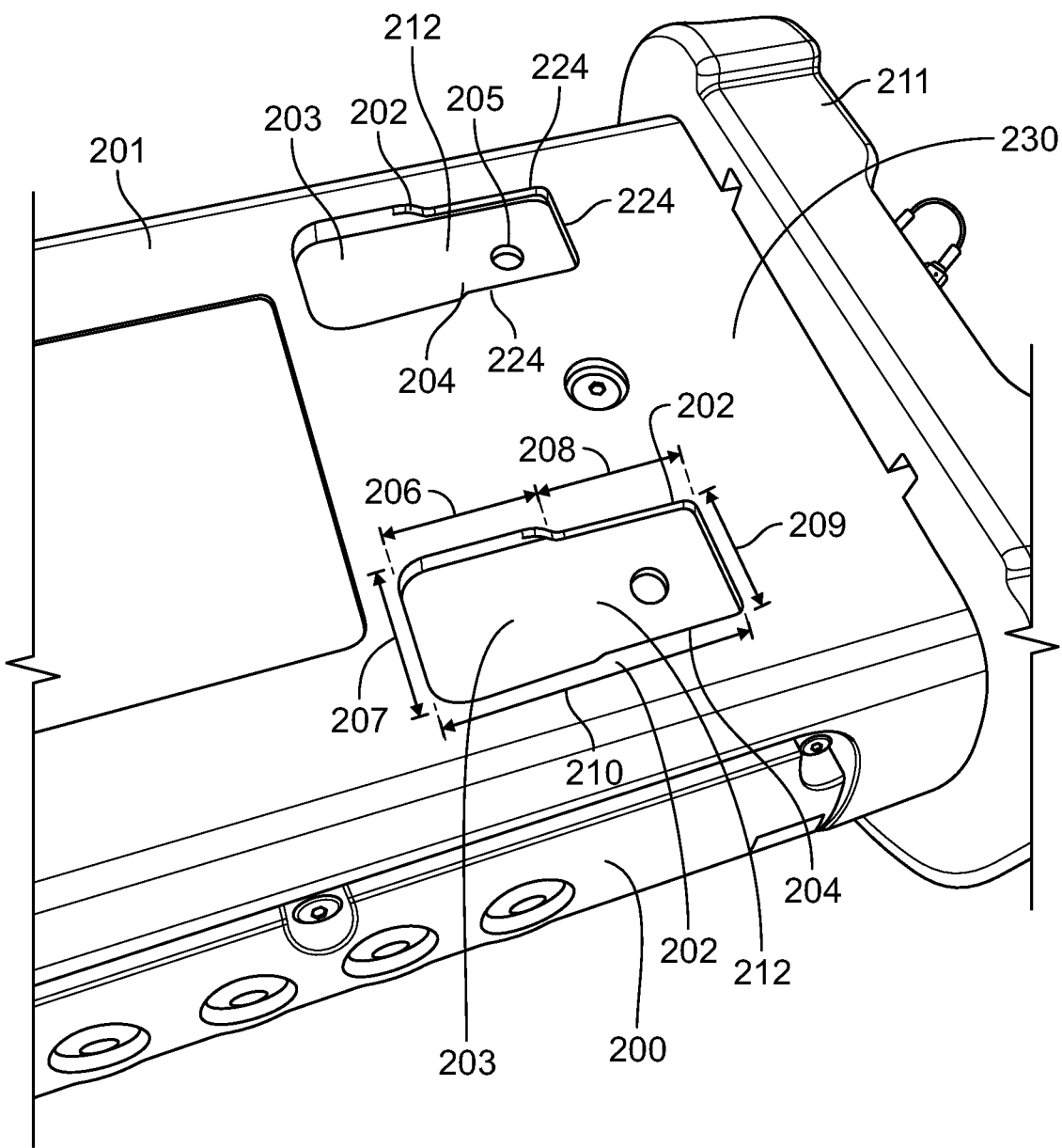
FIG. 2 is an illustration of a piece of equipment placed within equipment housing comprising a plurality of receiver sections in accordance with an embodiment of the present specification.

FIG. 2 illustrates a piece of equipment 200 placed within an equipment housing 201, wherein the equipment housing 201 comprises a plurality of receiver sections 202 in accordance with an embodiment of the present specification. In FIG. 2, equipment 200 is positioned within or inside equipment housing 201 that comprises a plurality of receiver sections 202. In FIG. 2, two receiver sections 202 are positioned on a first side section 230 of housing 201 and two additional receiver sections (not visible in FIG. 2) are symmetrically positioned on a second side section (not shown in FIG. 2, shown and described with respect to FIG. 4) of housing 201. In some embodiments, the equipment housing 201 further includes a rubber bumper 211 attached to first side section 230 and configured to protect the equipment housing 201 should it be accidentally dropped. The rubber bumper 211 is also configured to soften the effect of shock on internal components of equipment 200 positioned within equipment housing 201 should said housing 201 be accidentally dropped. In some embodiments, a second rubber bumper is attached to a second side section of the equipment housing 201 opposite the first side section 230.

In embodiments of the present specification, the number, shape and size of receiver sections configured in any equipment housing depend on the physical attributes of equipment to be placed within the housing. In embodiments, the number, shape and size of receiver sections configured in any equipment housing depend on the number, shape and size of corresponding mounting hangers used to mount the equipment and equipment housing. In embodiments, the number, shape and size of receiver sections of equipment housing and the number, shape and size of corresponding mounting hangers are customized based on the type of equipment to be mounted.

In embodiments, the equipment or the functional electronics residing inside or within any equipment housing are unique to that particular housing. In embodiments, the shape and size of the housing vary depending upon the unique functional electronics positioned inside the housing.

In some embodiments, the equipment housing and the corresponding mounting hangers are not unique for a particular piece of equipment and are standardized for a range of equipment.

The equipment housing 201 in FIG. 2 comprises four receiver sections 202; however, one can appreciate that the number of receiver sections configured in the equipment housing 201 may vary depending on the specific application and requirement. In an embodiment, each receiver section 202 comprises a first section, opening, or cutout opening 203 and a second section or locking access area 204 having a base 212. In embodiments, a t-slot shaped protrusion (shown as coupling portion 105 in FIG. 1A and 165 in FIG. 1C) of a mounting hanger is received in the cutout opening 203 and is then slid in the direction of locking access area 204 to mate with said locking access area 204. The edges 224 of the locking access area 204 comprise a t-slot for receiving the t-slot shaped protrusion of the coupling portion. In some embodiments, the receiver section opening or cutout opening 203 is sized larger than the locking access area 204 and does not include a t-slot. Once the coupling portion settles into the locking access area 204, the mounting hanger is considered to be in a final mated position in the receiver section 202. Subsequently, a spring loaded plunger lock present on the mounting hanger automatically engages to lock the mounting hanger with the locking access area 204 of receiver section 202. The base 212 of the locking access area 204 of the receiver section 202 comprises an accommodating hole 205 to receive a section of the plunger lock (shown as locking section 104a in FIG. 1A and 164a in FIG. 1C) which locks the two units and prevents the mounting hanger from disengaging itself from the equipment. In various embodiments, the hole 205 comprises any one of a void, indentation, or space that can receive, and physically engage, with a member, wherein the member comprises a portion of a plunger lock. In one embodiment, the only way for a t-slot shaped protrusion (shown as coupling portion 105 in FIG. 1A and 165 in FIG. 1C) of a mounting hanger to engage with the second section or locking access area 204 is to first be received in the first section or opening/cutout opening 203 and then be slid into place. The protrusion cannot be directly engaged with the second section or locking access area 204 without first being engaged with the first section or opening/cutout opening 203.

In embodiments, the base 212 of the receiver section 202 is slightly depressed from a surrounding surface level of the equipment housing 201, which helps in locking the mounting hanger with the receiver section 202 and prevents any unwanted movement. In some embodiments, the base 212 is depressed by 0.152 inches from the surrounding surface level of the equipment housing 201.

In some embodiments, shapes of cutout opening 203 and locking access area 204 are square with rounded corners. In an embodiment, length 206 and width 207 of the cutout opening 203 are equal to 0.750 inches and 0.750 inches respectively. In an embodiment, length 208 and width 209 of the locking access area 204 are equal to 0.630 inches and 0.630 inches respectively. In embodiments, dimensions of the cutout opening 203 and the locking access area 204 are different. The complete length 210 of the receiver section 202 is equal to the sum of length 206 and length 208.

In FIG. 2, a specific embodiment of the receiver section 202 is described which comprises a first substantially rectangular section 203 and a second substantially rectangular section 204. In alternate embodiments, the receiver section is configured in different shapes and sizes but is configured to receive and accommodate a portion of a mounting hanger having a spring loaded plunger locking mechanism to lock the hanger with the equipment housing.

In embodiments, the coupling portion 105, 165 of the mounting hanger 100, 160 shown in FIGS. 1A and 1C has a symmetrical shape and a same shape as locking access area 204 configured in the receiver section 202 of equipment housing 201. The locking access area 204 is sized slightly larger than the coupling portion 105, 165 such that the t-slot shaped protrusion of the coupling portion 105, 165 is capable of sliding into the t-slot shaped edges 224 of the locking access area 204, securely coupling the hanger to the receiver section.

Figure 3:
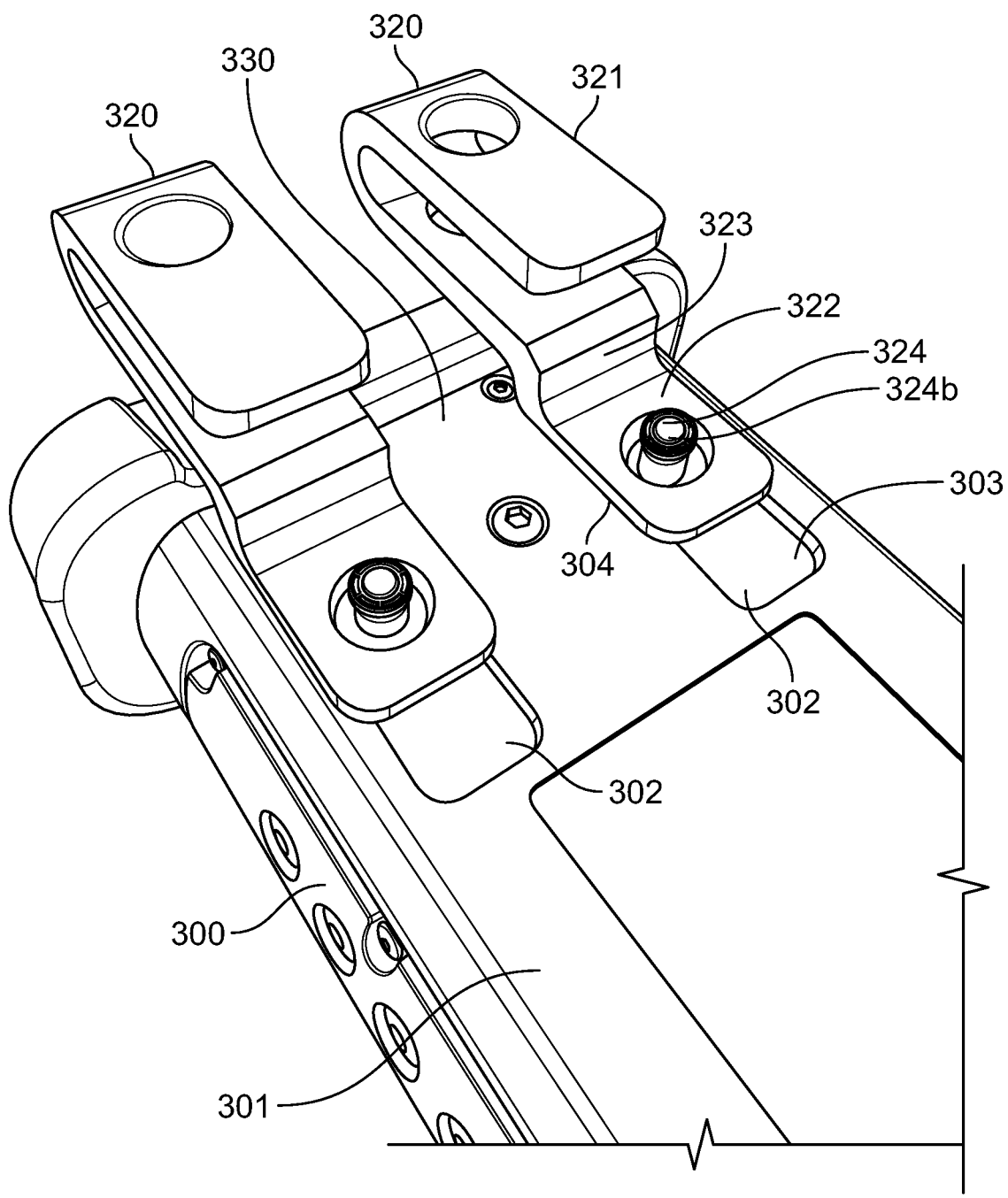
FIG. 3 illustrates a piece of equipment within an equipment housing coupled to a pair of mounting hangers in a vertical orientation, in accordance with an embodiment of the present specification.

FIG. 3 illustrates a piece of equipment 300 within an equipment housing 301 coupled in a vertical orientation with a pair of mounting hangers 320, in accordance with an embodiment of the present specification. As shown in FIG. 3, equipment 300 is positioned within or inside equipment housing 301 that comprises a plurality of receiver sections 302. In FIG. 3, two receiver sections 302 are positioned on a first side section 330 of housing 301 and two additional receiver sections (not visible in FIG. 3) are symmetrically positioned on second side section (not shown) of housing 301.

In embodiments of the present specification, the number, shape, size and strength of receiver sections configured in any equipment housing depend on the structure, shape, size, strength of corresponding mounting hangers. In embodiments, the number, shape, size and strength of receiver sections of housing and the structure, shape, size and strength of corresponding mounting hangers are customized based on the type of equipment to be mounted.

Each of the two receiver sections 302 that are visible in FIG. 3 is coupled to a corresponding mounting hanger 320. In the embodiment shown in FIG. 3, each of the mounting hangers 320 comprises a hook portion 321 connected to a straight portion 322 through a connecting portion 323. In embodiments, the hook portion 321 of each mounting hanger is used for hanging the respective mounting hanger with a surgical bed rail, IV pole or other supporting structure. The straight portion 322 comprises a means to connect the mounting hanger with a corresponding receiver section of equipment housing. In an embodiment, the straight portion 322 comprises a spring based plunger lock 324 which is adapted to engage with an accommodating hole or opening in a corresponding receiver section of housing and lock the mounting hanger 320 to the housing.

In embodiments, a coupling portion (shown as 105 in FIG. 1A and 165 in FIG. 1C) of the straight portion 322 of hanger 320 is received in a first section or cutout opening 303 of the receiver section 302. Subsequently, the hanger 320 is slid in a direction of a second section or locking access area 304 of the receiver section 302 until the coupling portion of straight portion 322 settles into the locking access area 304. Once the coupling portion of straight portion 322 is in with the locking access area 304, the spring loaded plunger lock 324 automatically engages with the second section 304 and locks the mounting hanger 320 with the equipment housing 301. In embodiments, a locking section (shown as 104a in FIG. 1A and 164a in FIG. 1C) present on an opposite side of the plunger lock handle 324b is received into a plunger accommodating hole (shown as 205 in FIG. 2) which locks the hanger 320 with the housing 301. In embodiments, the first section 303 is referred to as the cutout opening of the receiver section 302 in which a protruding section of mounting hanger is first received and the second section 304 is referred as the locking access area with which the protruding section of mounting hanger is mated, via t-slots as described above, for locking the same. In some embodiments, the first section or cutout opening 303 is sized larger than the second section or locking access area 304 and does not include a t-slot.

The spring plunger based locking mechanism disclosed in the present specification has significant benefits because of its ease of use. The spring loaded plunger lock automatically engages with a receiver section and locks a mounting hanger with the equipment housing. A user can also manually retract it to unlock the same. The spring loaded automatic plunger type of connecting mechanism disclosed in the present specification allows the user to change a position or orientation of equipment with ease. It solves significant problems that exist in current systems and methods followed for mounting equipment in medical rooms. In most of the commercially available mounting solutions, a bed rail hanger is permanently fixed to the equipment housing and cannot be user adjusted or optimized in any way. In mounting systems that do provide a limited degree of flexibility in changing a position of the mounted equipment, the process of removal and repositioning of the equipment is a highly cumbersome. The equipment is coupled to mounting hangers through fastening means such as screws and nuts, which makes the process of attaching/detaching the equipment from a mounting hanger very time consuming. The process involves tools to disengage the fastening means and detach the equipment from the mounting hanger and then to attach the equipment to the mounting hanger in a different position and then reengage the fastening means.

Further, typical commercially available mounting hangers are not symmetrical about the connecting portion or the locking access area allowing the equipment to only be affixed in one specific orientation. A user cannot optimize the placement of medical equipment in an operating area or hospital room if the user is restricted to mounting the medical equipment in a specific orientation. In embodiments described in the present specification, the removal and re-orientation of mounting hangers is a tool-less and quick operation, able to be done intuitively by the user or technician.

In the embodiment shown in FIG. 3, two mounting hangers 320 are locked/coupled with two corresponding receiver sections 302. In embodiments, the number of mounting hangers used for mounting a piece of equipment may be different and depends on various factors including but not limited to weight, size and shape of the equipment and type and strength of the mounting hanger and the receiver sections.

In embodiments, the coupling portion (shown as 105 in FIG. 1A and 165 in FIG. 1C) of the mounting hanger 320 can be rotated symmetrically about an axis (shown as 150 in FIG. 1A) before being coupled with the locking access area 304 and is hence capable of being inserted or affixed in multiple orientations. This allows a piece of equipment being mounted to a surgical bed, IV pole or other support structure to be oriented in various ways, allowing a user to optimize the placement in a medical environment.

In embodiments, the mounting hangers 320 can be coupled to the equipment housing 301 in four different vertical orientations/positions. In the embodiment shown in FIG. 3, the mounting hangers are coupled to the equipment housing 301 in one specific vertical orientation. In a second alternative embodiment, the mounting hangers 320 can be rotated by 180 degrees (in the plane comprising the housing 301) and can still be coupled to the two receiver sections 302 visible in the FIG. 3 in a vertical orientation. Similarly, the mounting hangers 320 can be coupled in two more vertical orientations with the receiver sections 302 (not visible in FIG. 3) that are positioned on the second side section of the equipment housing 301.

Figure 4:
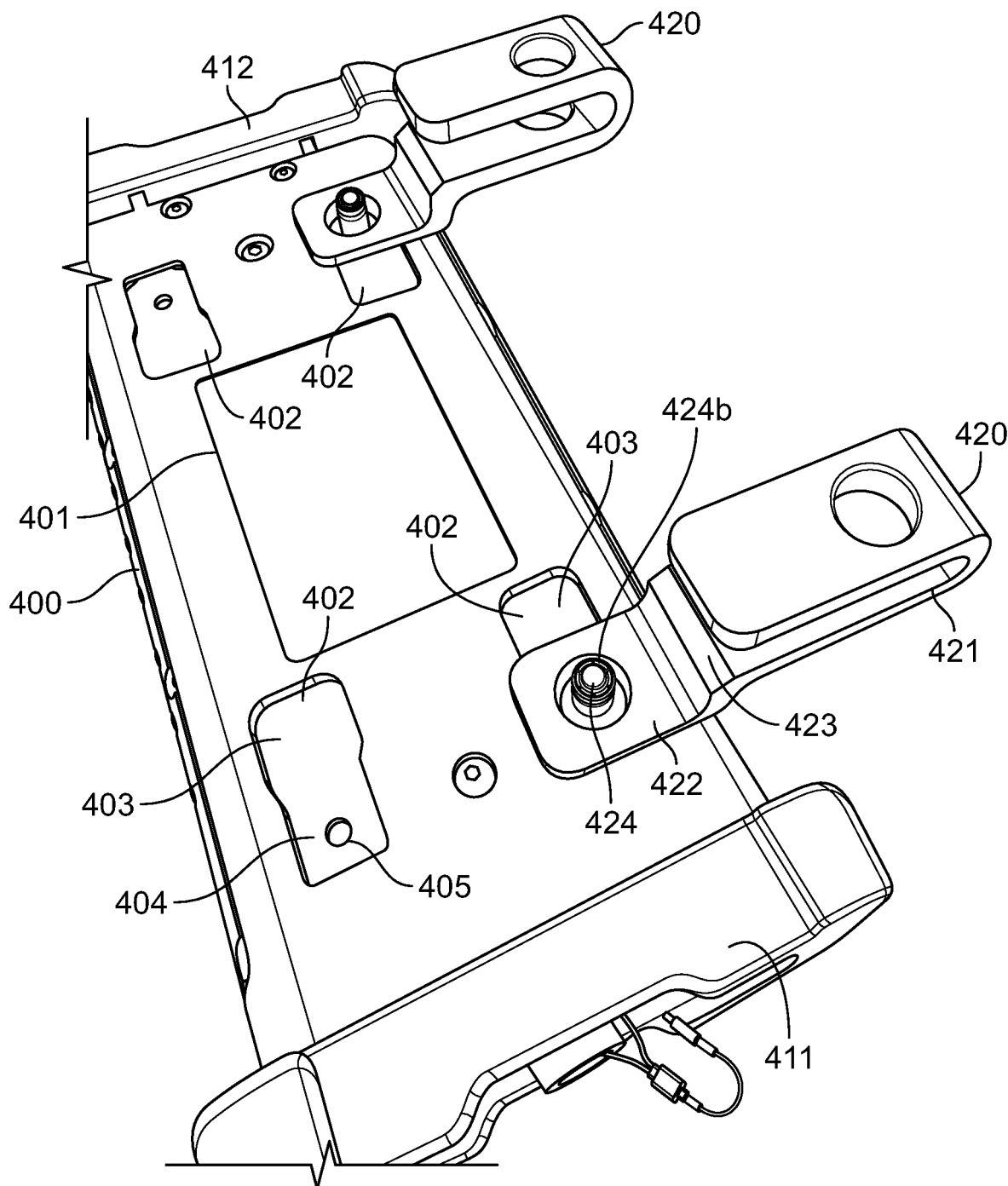
FIG. 4 shows a piece of equipment within an equipment housing coupled to a pair of mounting hangers in a horizontal orientation in accordance with an embodiment of the present specification.

FIG. 4 illustrates a piece of equipment 400 within an equipment housing 401 coupled in a horizontal orientation with a pair of mounting hangers 420, in accordance with an embodiment of the present specification. As shown in FIG. 4, a piece of equipment 400 is placed inside or within an equipment housing 401 that comprises a plurality of receiver sections 402. The equipment housing 401 includes first and second rubber bumpers 411, 412 attached to opposite sides or ends of the housing 401 to protect the housing 401 and equipment 400 should the housing 401 be dropped accidentally. In FIG. 4, four receiver sections 402 are shown, each of which is equipped to receive and connect with a corresponding mounting hanger. In some embodiments, only one of the receiver sections 402 is coupled to a corresponding mounting hanger to mount the equipment 400. In the embodiment shown in FIG. 4, two receiver sections 402 are shown connected to corresponding mounting hangers 420 to mount the equipment 400. The number of mounting hangers used for mounting a specific piece of equipment depends on a variety of factors including but not limited to weight, volume and other dimensions of the equipment and the structure, strength and type of mounting hanger and receiver sections.

In the embodiment shown in FIG. 4, each of the mounting hangers 420 comprises a hook portion 421 connected to a straight portion 422 through a connecting portion 423. In embodiments, the hook portion 421 of each mounting hanger is used for hanging the respective mounting hanger with a surgical bed rail, IV pole or other supporting structures. The straight portion 422 comprises means for connecting the mounting hanger with a corresponding receiver section 402 of equipment housing 401. In an embodiment, the straight portion 422 comprises a spring based plunger lock 424 which is adapted to engage with an accommodating hole or opening 405 in the corresponding receiver section 402 of equipment housing and lock the mounting hanger 420 with the equipment housing.

In FIG. 4, the straight portion 422 of each hanger 420 is in a locking access area 404 of a corresponding receiver section 402. In embodiments, a coupling portion (shown as 105 in FIG. 1A and 165 in FIG. 1C) of the straight portion 422 of hanger 420 is received in a first section or cutout opening 403 of the receiver section 402. Subsequently, the hanger 420 is slid in a direction of second section or locking access area 404 of the receiver section 402 until the coupling portion of straight portion 422 settles into the locking access area 404. The locking access area 404 further comprises a t-slot for receiving the t-slot shaped protrusion of the coupling portion. Once the coupling portion of straight portion 422 is in the locking access area 404, the spring loaded plunger lock 424 automatically engages with the second section 404 and locks the mounting hanger 420 with the equipment housing 401. In embodiments, a locking section (shown as 104a in FIG. 1A and 164a in FIG. 1C) present on an opposite side of the plunger handle 424b is received into a plunger accommodating hole (shown as 205 in FIG. 2) which locks the hanger 420 with the housing 401. In some embodiments, the first section or cutout opening 403 is sized larger than the second section or locking access area 404 and does not include a t-slot.

In embodiments, the coupling portion (shown as 105 in FIG. 1A and 165 in FIG. 1C) of the mounting hanger 420 can be rotated about an axis (shown as 150 in FIG. 1A) before being coupled with the locking access area and is hence capable of being inserted in multiple orientations. This allows the equipment being mounted to a surgical bed, IV pole or other support structure to be oriented in various ways, allowing a user to optimize the placement in a medical environment. In embodiments, the mounting hangers 420 can be coupled to equipment housing 401 in four different horizontal orientations/positions. In the embodiment shown in FIG. 4, the mounting hangers are coupled to the equipment housing in one specific horizontal orientation. In a second alternative embodiment, the mounting hangers 420 can be rotated by 180 degrees (in the plane comprising the housing 401 and can still be coupled to the same two receiver sections 402 with which the mounting hangers 420 are currently connected. Similarly, the mounting hangers 420 can be coupled in two more horizontal orientation to the two other receiver sections 402 that are configured on the other end of the equipment housing 401.

Figure 5:
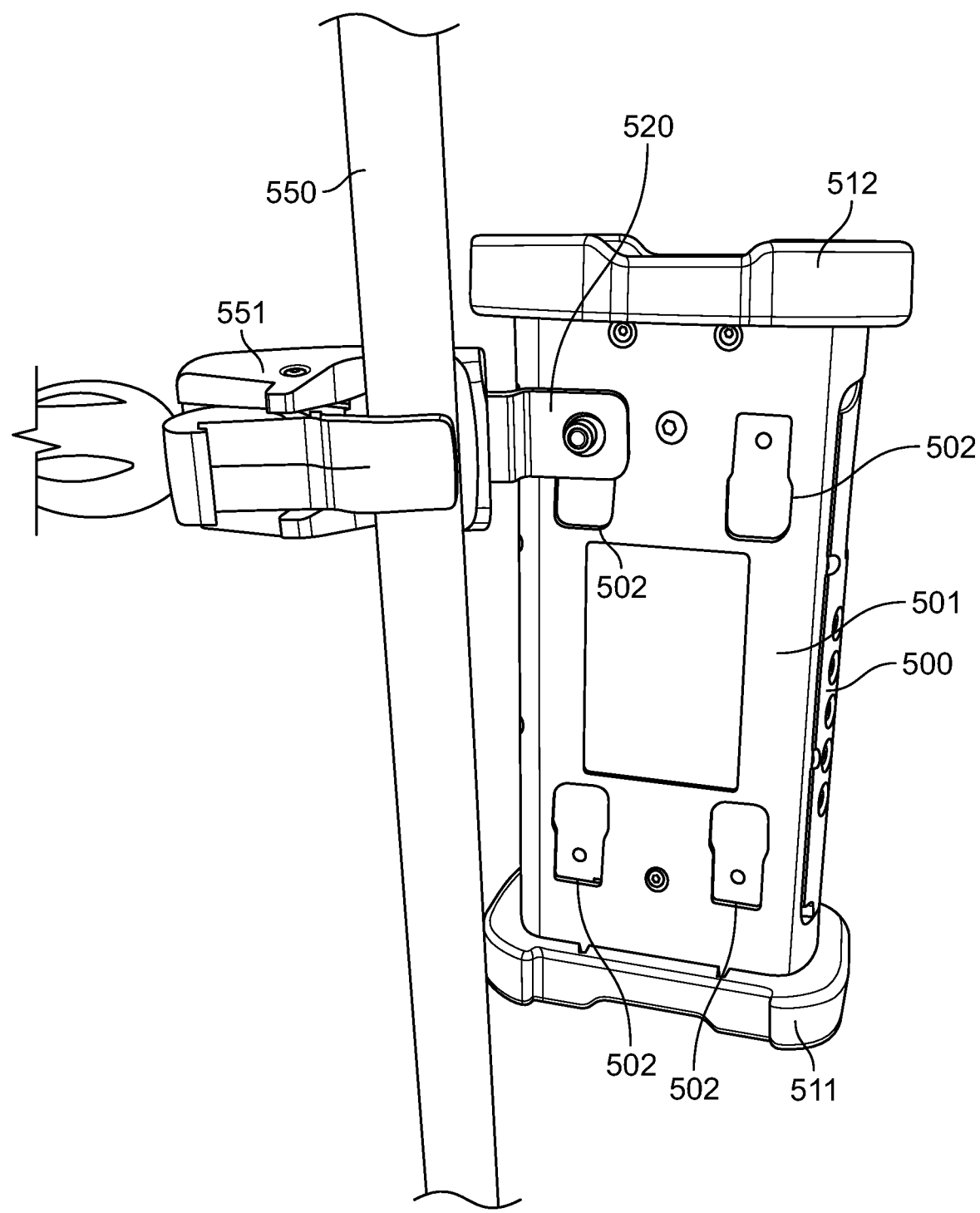
FIG. 5 shows a piece of equipment mounted on an IV pole in conjunction with a mounting hanger in accordance with an embodiment of the present specification.

FIG. 5 illustrates a piece of equipment 500 mounted on an IV pole 550 with the assistance of a mounting hanger 520 in accordance with an embodiment of the present specification. As shown in FIG. 5, equipment 500 is placed inside an equipment housing 501 that comprises a plurality of receiver sections 502. The equipment housing 501 includes first and second rubber bumpers 511, 512 attached to opposite sides or ends of the housing 501 to protect the housing 501 and equipment 500 should the housing 501 be dropped accidentally. The equipment housing 501, through one of its receiver sections 502, is coupled to a mounting hanger 520 which is further coupled to a pole 550. In embodiments, a hook portion (not visible in FIG. 5) of a mounting hanger 520 is hooked/hanged with a connecting portion or clamp 551 of the pole 550 to mount the mounting hanger 520 and thereby the equipment housing 501 on the pole 500.

In the embodiment shown in FIG. 5, only one mounting hanger and one corresponding receiver section is used for mounting the equipment 500 on the pole 550. However, one can observe in FIG. 5 that probably one mounting hanger is not enough to mount the equipment 500 as entire equipment housing 501 is in a slightly tilted/unstable position and the lower portion of the equipment housing 501 is touching the pole 550. To avoid this problem, in embodiments, one more mounting hanger can be deployed between the equipment housing 501 and the pole 550 to provide stability to the system. Preferably, a receiver section that is positioned vertically below the receiver section already coupled with the mounting hanger 520 in above embodiment is used to mount a second hanger.

Figure 6:
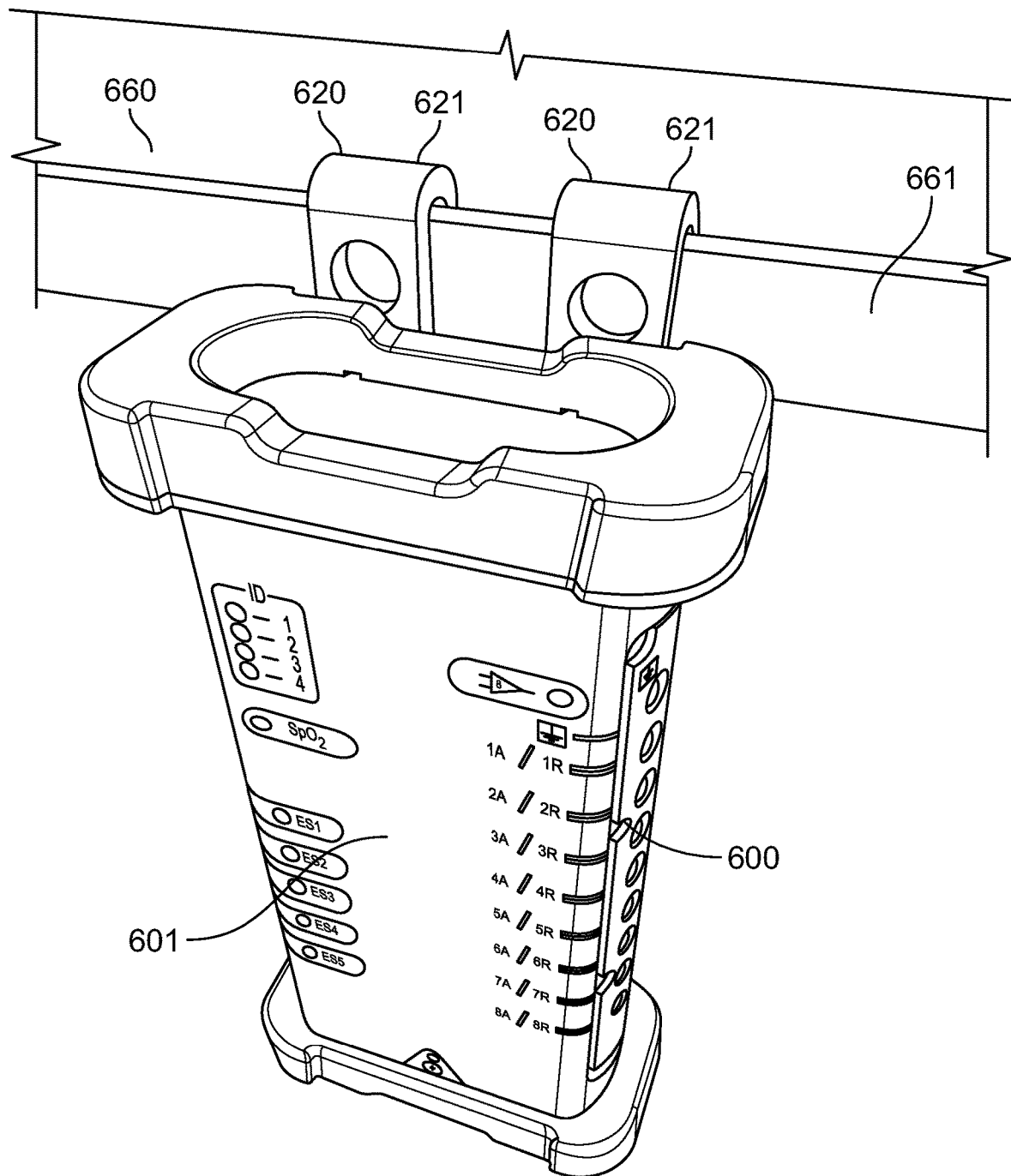
FIG. 6 shows a piece of equipment mounted on bed rails with the assistance of mounting hangers in accordance with an embodiment of the present specification.

FIG. 6 illustrates a piece of equipment 600 mounted on bed rails 661 with the assistance of mounting hangers in accordance with an embodiment of the present specification. As shown in FIG. 6, a piece of equipment 600 is placed inside an equipment housing 601 that comprises a plurality of receiver sections. The equipment housing 601, through two of its receiver sections, is coupled to two mounting hangers 620 which are further coupled to a bed rail 661 of a bed 660. In embodiments, the hook portions 621 of the mounting hangers 620 are hooked/hanged with the bed rail 661 of the bed 660.

Figure 7A:
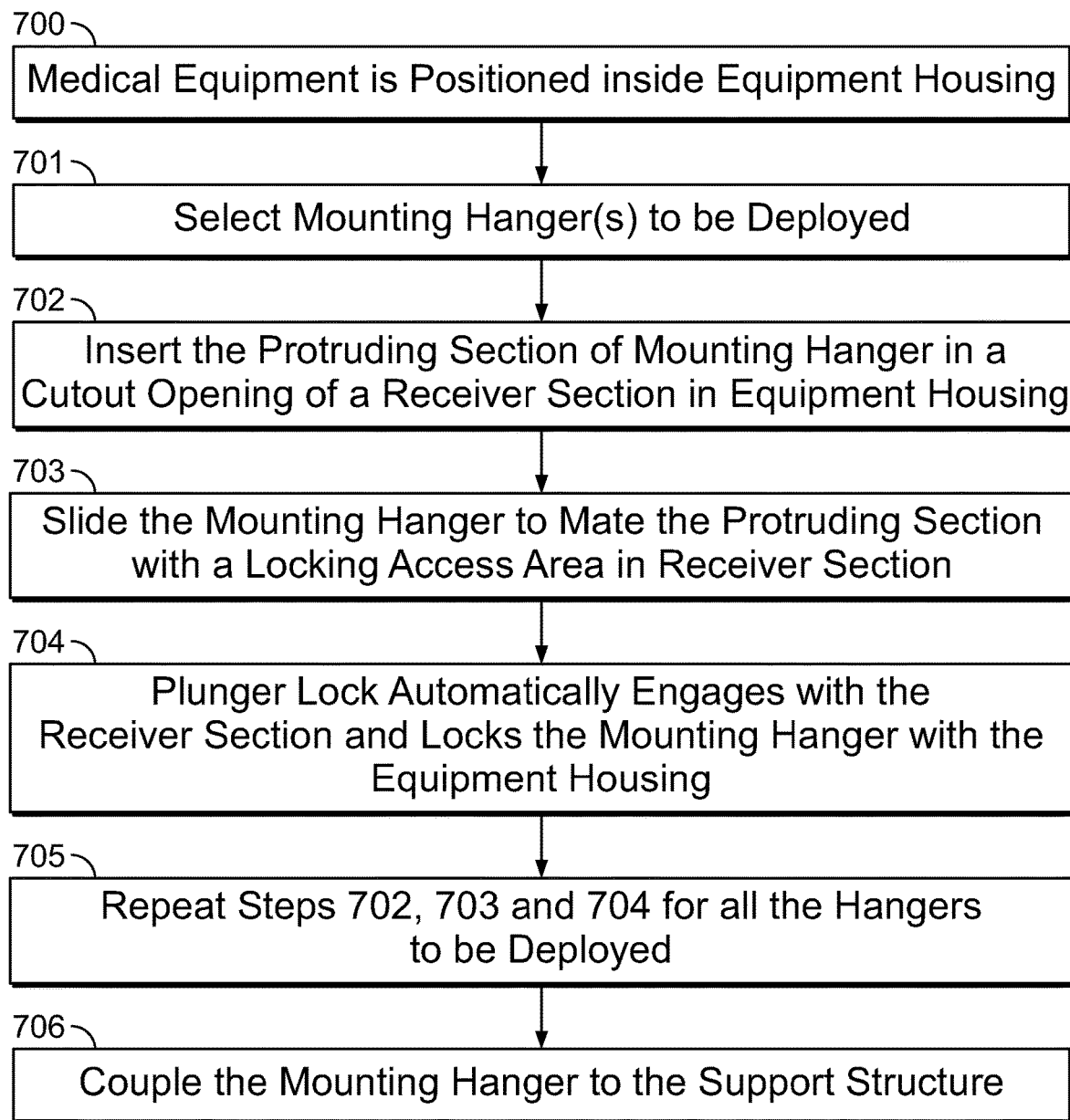
FIG. 7A is a flowchart illustrating steps for mounting a piece of equipment on a support structure in accordance with an embodiment of the present specification.

FIG. 7A is a flowchart illustrating the steps followed to mount a piece of medical equipment on a support structure in accordance with an embodiment of the present specification. As shown in FIG. 7A, at step 700, the medical equipment is positioned inside an equipment housing. At step 701, a user selects mounting hangers required to mount a particular piece of equipment. In embodiments, the selection of mounting hangers, including type and number of mounting hangers, depends on the equipment housing used for a specific piece of equipment. In embodiments, the selection of mounting hangers is also dependent on the attributes of the corresponding equipment, including weight, volume and other physical dimensions of the equipment. At step 702, the user inserts a t-slot symmetrical protruding section of the first selected mounting hanger in a cutout opening in a receiver section of the equipment housing. At step 703, the user slides the mounting hanger to mate the t-slot section with a locking access area in the receiver section. At step 704, a spring loaded plunger lock automatically engages with the receiver section and locks the mounting hanger with the equipment housing. At step 705, the steps 702, 703 and 704 are repeated for connecting each selected mounting hanger with a corresponding receiver section in the equipment housing. At step 706, each mounting hanger is coupled to the support structure. In some embodiments, hook portions of all connected mounting hangers, such as the mounting hanger depicted in FIG. 1A, are hanged on a support structure to mount the equipment on the support structure. In other embodiments, the mounting hangers include openings or screw holes, such as the mounting hanger depicted in FIG. 1C, for coupling the mounting hanger to a clamp, which is then, in turn, coupled to the support structure. Optionally, in other embodiments, step 706 is performed before steps 702 through 705.

Figure 7B:
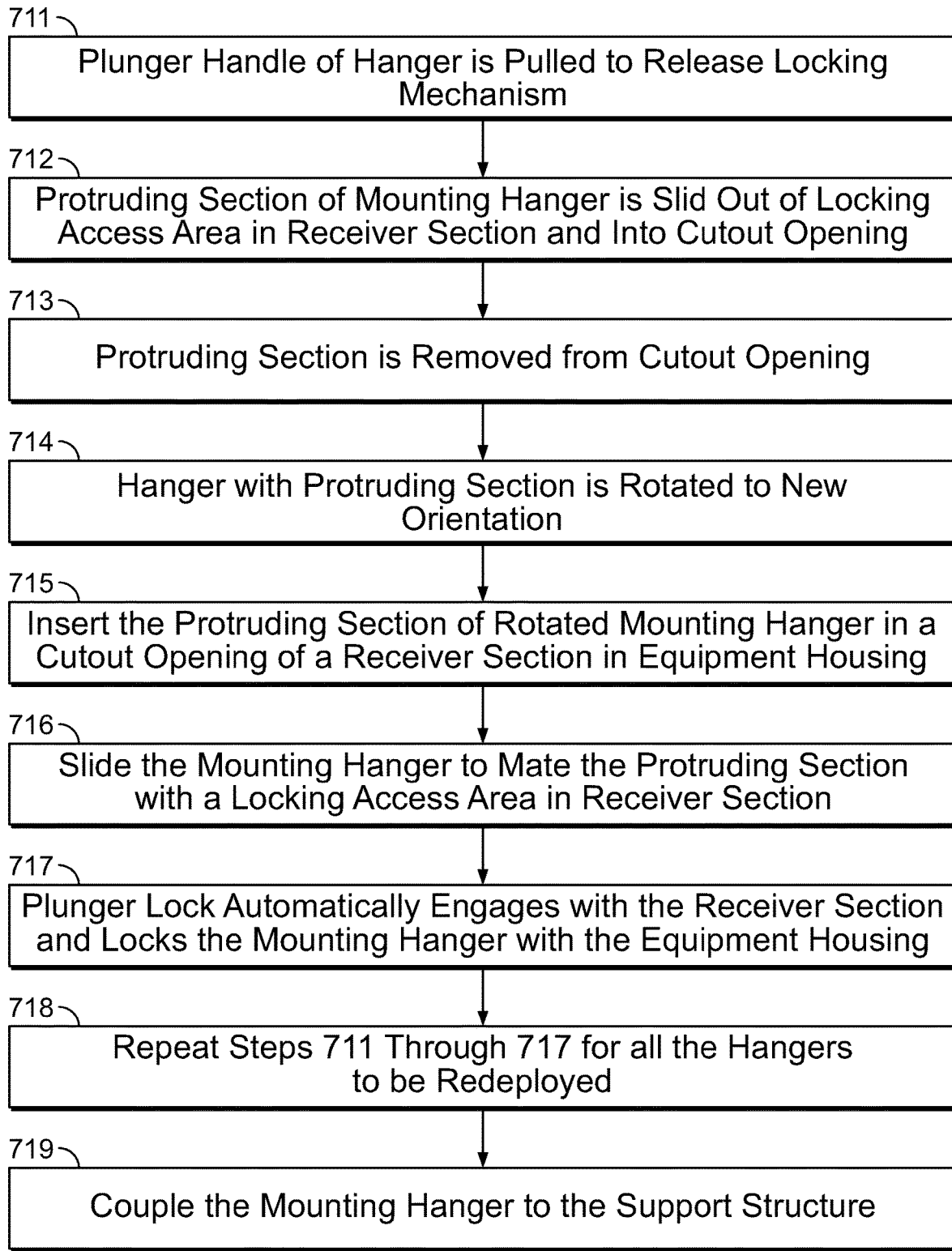
FIG. 7B is a flowchart illustrating the steps followed to remount a piece of equipment on a support structure in a new orientation, in accordance with an embodiment of the present specification.

FIG. 7B is a flowchart illustrating the steps followed to remount a piece of equipment on a support structure in a new orientation, in accordance with an embodiment of the present specification. As shown in FIG. 7B, at step 711, a user pulls on a plunger handle of a mounting hanger to release the locking mechanism. The user then slides the protruding section of the mounting hanger out of the locking access area in the receiver section and into the cutout opening at step 712. The protruding section is removed from the cutout opening at step 713. The user then rotates the hanger with protruding section to a new orientation at step 714. At step 715, the user inserts the t-slot symmetrical protruding section of the rotated mounting hanger in a cutout opening in a receiver section of the equipment housing. At step 716, the user slides the mounting hanger to mate the t-slot section with a locking access area in the receiver section. At step 717, a spring loaded plunger lock automatically engages with the receiver section and locks the mounting hanger with the equipment housing. At step 718, the steps 711 through 717 are repeated for connecting each selected mounting hanger to be redeployed with a corresponding receiver section in the equipment housing. At step 719, hook portions of all connected mounting hangers are hanged on a support structure to mount the equipment on the support structure. At step 719, each mounting hanger is coupled to the support structure. In some embodiments, hook portions of all connected mounting hangers, such as the mounting hanger depicted in FIG. 1A, are hanged on a support structure to mount the equipment on the support structure. In other embodiments, the mounting hangers include openings or screw holes, such as the mounting hanger depicted in FIG. 1C, for coupling the mounting hanger to a clamp, which is then, in turn, coupled to the support structure. Optionally, in other embodiments, step 719 is performed before steps 711 through 718.

In an embodiment, the equipment mounting hanger of the present specification is used for mounting a cortical amplifier (such as Cadwell Cortical Amplifier). The cortical amplifier is used during surgical procedures and is typically mounted to the surgical bed rails. The cortical amplifier utilizes multiple patient connected leads as well as power and communication cables which are routed back to the operator/technician who is usually located at some distance from the surgical table.

In an embodiment, using the equipment mounting solution disclosed in the present specification, the operator/technician can find the best location on the surgical bed rail and can mount the cortical amplifier positioned inside an equipment housing of the present specification through a mounting hanger. This ensures that the device itself, along with any attached leads and cables are secure and routed most efficiently for a given procedure. The multiple mounting configurations/orientations available through the mounting system disclosed in present specification allows for the most efficient routing of the communication and power cables, as well as the patient connected leads.

The foregoing is merely illustrative of the principles of the disclosure, and the systems, devices, and methods can be practiced by other than the described embodiments, which are presented for purposes of illustration and not of limitation.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The above examples are merely illustrative of the many applications of the system of the present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of mounting medical equipment on a support structure comprising:

acquiring a housing comprising at least one receiver section, wherein the housing is configured to receive the medical equipment;

coupling at least one mounting device with the at least one receiver section in the housing, wherein coupling the mounting device with the at least one receiver section comprises inserting a portion of the mounting device into a portion of the at least one receiver section and mating the portion of the mounting device with a locking area in the at least one receiver section, wherein, as the portion of the mounting device is inserted into a final mated position with the locking area, a plunger lock located on the at least one mounting device automatically engages with a portion of the at least one receiver section to lock the at least one mounting device with the at least one receiver section; and coupling the at least one mounting device with the support structure.

2. The method of claim 1, wherein the support structure is a pole.

3. The method of claim 1, wherein the support structure is a bed frame.

4. The method of claim 1, further comprising decoupling the at least one mounting device from the support structure.

5. The method of claim 4, wherein decoupling the at least one mounting device from the support structure comprises pulling a portion of the plunger lock to cause an opposing portion of the plunger lock to disengage from the at least one receiver section.

6. The method of claim 5, wherein the plunger lock comprises a spring and wherein the spring is configured to cause the opposing portion of the plunger lock to engage with the at least one receiver section.

7. The method of claim 1, wherein coupling at least one mounting device with the at least one receiver section in the housing further comprises inserting the mounting device into an open end of the least one receiver section and sliding the at least one mounting device along the least one receiver section until a portion of the plunger lock automatically extends into the at least one receiver section.

8. The method of claim 1, wherein coupling the at least one mounting device with the support structure comprises coupling a hook portion of a hanger in the at least one mounting device with the support structure and a substantially straight portion wherein the substantially straight portion comprises a protruding section and the plunger lock.

9. The method of claim 8, wherein coupling at least one mounting device with the at least one receiver section in the housing comprises positioning the protruding section in a final mated position within the locking area, and centering the plunger lock over an accommodating hole in the at least one receiver section to automatically engage therein, thereby locking the mounting device with the at least one receiver section.

10. A method of mounting medical equipment on a support structure comprising:
   acquiring a housing comprising at least one receiver section having an opening integrated within a surface of the at least one receiver section, wherein the housing is configured to receive the medical equipment;
   coupling at least one mounting device with the at least one receiver section in the housing, wherein the at least one mounting device has a first orientation, a second orientation, a third orientation, and a fourth orientation, wherein the first orientation is perpendicular to the second orientation and the third orientation is perpendicular to the fourth orientation, and wherein coupling the mounting device with the at least one receiver section comprises:
      inserting a portion of the at least one mounting device into a portion of the at least one receiver section; and
      mating the portion of the at least one mounting device with the opening in the at least one receiver section, wherein, as the portion of the at least one mounting device is inserted into a final mated position with the opening, a lock positioned on the at least one mounting device automatically engages with the opening of the at least one receiver section to lock the at least one mounting device with the at least one receiver section and wherein the at least one mounting device is configured to be inserted and locked into the at least one receiver section in any of the first, second, third, or fourth orientations; and
   coupling the at least one mounting device with the support structure.

11. The method of claim 10, wherein the support structure is a pole.

12. The method of claim 10, wherein the support structure is a bed frame.

13. The method of claim 10, further comprising decoupling the at least one mounting device from the support structure.

14. The method of claim 13, wherein the lock is a plunger lock and decoupling the at least one mounting device from the support structure comprises pulling a portion of the plunger lock to cause an opposing portion of the plunger lock to disengage from the opening of the at least one receiver section.

15. The method of claim 14, wherein the plunger lock comprises a spring and wherein the spring is configured to cause the opposing portion of the plunger lock to engage with the opening of the at least one receiver section.

16. The method of claim 10, wherein coupling at least one mounting device with the at least one receiver section in the housing comprises inserting the mounting device into an open end of the least one receiver section and sliding the at least one mounting device along the least one receiver section until a portion of the lock automatically extends into the at least one receiver section.

17. The method of claim 10, wherein coupling the at least one mounting device with the support structure comprises coupling a hook in the at least one mounting device to the support structure and a substantially straight portion wherein the substantially straight portion comprises a protruding section and the lock.

18. The method of claim 17, wherein mating the portion of the at least one mounting device with the opening in the at least one receiver section comprises positioning the protruding section in a final mated position within the locking area such that the lock is configured to be centered over the opening in the at least one receiver section and automatically engage therein, thereby locking the mounting device with the at least one receiver section.

* * * * *